United States Patent
Hughes et al.

(10) Patent No.: US 6,466,644 B1
(45) Date of Patent: Oct. 15, 2002

(54) METHOD AND SYSTEM FOR VERIFICATION OF DIFFERENT TYPES OF BEAM LIMITING DEVICES IN A LINEAR ACCELERATOR UTILIZED FOR RADIOTHERAPY

(75) Inventors: John H. Hughes, Martinez; Francisco M. Hernandez-Guerra, Concord, both of CA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 70 days.

(21) Appl. No.: 09/596,791

(22) Filed: Jun. 19, 2000

Related U.S. Application Data
(60) Provisional application No. 60/158,333, filed on Oct. 6, 1999.

(51) Int. Cl.[7] .................................................. A61N 5/10
(52) U.S. Cl. ........................ 378/65; 378/150; 378/152
(58) Field of Search ........................... 378/65, 64, 145, 378/147, 149, 150, 151, 152, 153, 148; 250/492.1, 492.3

(56) References Cited

U.S. PATENT DOCUMENTS
5,555,283 A * 9/1996 Shiu et al. .................. 378/151
5,654,996 A * 8/1997 Steinberg et al. ............. 378/65

OTHER PUBLICATIONS
WPI Abstract Accession No. 1988–183973 & DE 3643902A (Bulcher).

* cited by examiner

*Primary Examiner*—Robert H. Kim

(57) ABSTRACT

Aspects for verifying an accessory beam limiting device position for a radiotherapy treatment session are described. Included in a system aspect is a radiotherapy treatment device, the radiotherapy treatment device including an accessory holder. A beam limiting device for establishing a treatment area, the beam limiting device held in the accessory holder, is also included, along with a first controller for controlling the radiotherapy device and performing a treatment plan. A second controller positions the beam limiting device according to the treatment plan, wherein performance of the treatment plan by the first controller depends on provision of an accessory code to the first controller. The accessory code includes a resistor-pair combination value.

16 Claims, 4 Drawing Sheets

| | | RB | | | | | | | | |
|---|---|---|---|---|---|---|---|---|---|---|
| Ohms | 5.36K | 5.62K | 5.90K | 6.19K | 6.49K | 6.81K | 7.15K | 7.50K | 8.25K | |
| | MM0... | MM1... | MM2... | MM3... | MM4... | MM5... | MM6... | MM7... | MM8... | |
| RA | 8.66K | | | | | | | | | |

FIG. 2

| Ohms | | RA | | | | | | | | | | | | | |
|---|---|---|---|---|---|---|---|---|---|---|---|---|---|---|---|
| | Hex Counts | 1.00K | 1.24K | 1.50K | 1.74K | 2.00K | 2.21K | 2.49K | 2.74K | 3.09K | 3.32K | 3.65K | 3.92K | 4.22K |
| | | 333 | 395 | 3FF | 482 | 4CC | 522 | 595 | 5FB | 68B | 6E9 | 770 | 7DE | 859 |
| 1.00K | 333 | MM0001 | MM0027 | MM0053 | MM0079 | MM0105 | MM0131 | MM0157 | MM0183 | MM0209 | MM0235 | MM0261 | MM0287 | MM0313 |
| 1.24K | 395 | MM0002 | MM0028 | MM0054 | MM0080 | MM0106 | MM0132 | MM0158 | MM0184 | MM0210 | MM0236 | MM0262 | MM0288 | MM0314 |
| 1.50K | 3FF | MM0003 | MM0029 | MM0055 | MM0081 | MM0107 | MM0133 | MM0159 | MM0185 | MM0211 | MM0237 | MM0263 | MM0289 | MM0315 |
| 1.74K | 462 | MM0004 | MM0030 | MM0056 | MM0082 | MM0108 | MM0134 | MM0160 | MM0186 | MM0212 | MM0238 | MM0264 | MM0290 | MM0316 |
| 2.00K | 4CC | MM0005 | MM0031 | MM0057 | MM0083 | MM0109 | MM0135 | MM0161 | MM0187 | MM0213 | MM0239 | MM0265 | MM0291 | MM0317 |
| 2.21K | 522 | MM0006 | MM0032 | MM0058 | MM0084 | MM0110 | MM0136 | MM0162 | MM0188 | MM0214 | MM0240 | MM0266 | MM0292 | MM0318 |
| 2.49K | 595 | MM0007 | MM0033 | MM0059 | MM0085 | MM0111 | MM0137 | MM0163 | MM0189 | MM0215 | MM0241 | MM0267 | MM0293 | MM0319 |
| 2.74K | 5FB | MM0008 | MM0034 | MM0060 | MM0086 | MM0112 | MM0138 | MM0164 | MM0190 | MM0216 | MM0242 | MM0268 | MM0294 | MM0320 |
| 3.09K | 68B | MM0009 | MM0035 | MM0061 | MM0087 | MM0113 | MM0139 | MM0165 | MM0191 | MM0217 | MM0243 | MM0269 | MM0295 | MM0321 |
| 3.32K | 6E9 | MM0010 | MM0036 | MM0062 | MM0088 | MM0114 | MM0140 | MM0166 | MM0192 | MM0218 | MM0244 | MM0270 | MM0296 | MM0322 |
| 3.65K | 770 | MM0011 | MM0037 | MM0063 | MM0089 | MM0115 | MM0141 | MM0167 | MM0193 | MM0219 | MM0245 | MM0271 | MM0297 | MM0323 |
| 3.92K | 7DE | MM0012 | MM0038 | MM0064 | MM0090 | MM0116 | MM0142 | MM0168 | MM0194 | MM0220 | MM0246 | MM0272 | MM0298 | MM0324 |
| 4.22K | 859 | MM0013 | MM0039 | MM0065 | MM0091 | MM0117 | MM0143 | MM0169 | MM0195 | MM0221 | MM0247 | MM0273 | MM0299 | MM0325 |
| 4.48K | 8C4 | MM0014 | MM0040 | MM0066 | MM0092 | MM0118 | MM0144 | MM0170 | MM0196 | MM0222 | MM0248 | MM0274 | MM0300 | MM0326 |
| 4.75K | 932 | MM0015 | MM0041 | MM0067 | MM0093 | MM0119 | MM0145 | MM0171 | MM0197 | MM0223 | MM0249 | MM0275 | MM0301 | MM0327 |
| 5.11K | 9C6 | MM0016 | MM0042 | MM0068 | MM0094 | MM0120 | MM0146 | MM0172 | MM0198 | MM0224 | MM0250 | MM0276 | MM0302 | MM0328 |
| 5.36K | A2C | MM0017 | MM0043 | MM0069 | MM0095 | MM0121 | MM0147 | MM0173 | MM0199 | MM0225 | MM0251 | MM0277 | MM0303 | MM0329 |
| 5.62K | A96 | MM0018 | MM0044 | MM0070 | MM0096 | MM0122 | MM0148 | MM0174 | MM0200 | MM0226 | MM0252 | MM0278 | MM0304 | MM0330 |
| 5.90K | B09 | MM0019 | MM0045 | MM0071 | MM0097 | MM0123 | MM0149 | MM0175 | MM0201 | MM0227 | MM0253 | MM0279 | MM0305 | MM0331 |
| 6.19K | B81 | MM0020 | MM0046 | MM0072 | MM0098 | MM0124 | MM0150 | MM0176 | MM0202 | MM0228 | MM0254 | MM0280 | MM0306 | MM0332 |
| 6.49K | BFB | MM0021 | MM0047 | MM0073 | MM0099 | MM0125 | MM0151 | MM0177 | MM0203 | MM0229 | MM0255 | MM0281 | MM0307 | MM0333 |
| 6.81K | C7E | MM0022 | MM0048 | MM0074 | MM0100 | MM0126 | MM0152 | MM0178 | MM0204 | MM0230 | MM0256 | MM0282 | MM0308 | MM0334 |
| 7.15K | D09 | MM0023 | MM0049 | MM0075 | MM0101 | MM0127 | MM0153 | MM0179 | MM0205 | MM0231 | MM0257 | MM0283 | MM0309 | MM0335 |
| 7.50K | D98 | MM0024 | MM0050 | MM0076 | MM0102 | MM0128 | MM0154 | MM0180 | MM0206 | MM0232 | MM0258 | MM0284 | MM0310 | MM0336 |
| 8.25K | ECB | MM0025 | MM0051 | MM0077 | MM0103 | MM0129 | MM0155 | MM0181 | MM0207 | MM0233 | MM0259 | MM0285 | MM0311 | MM0337 |
| 8.66K | F73 | MM0026 | MM0052 | MM0078 | MM0104 | MM0130 | MM0156 | MM0182 | MM0208 | MM0234 | MM0260 | MM0286 | MM0312 | MM0338 |

(RB labels the leftmost Ohms column)

FIG. 3a

| Ohms | | 4.48K | 4.75K | 5.11K | 5.36K | 5.62K | 5.90K | 6.19K | 6.49K | 6.81K | 7.15K | 7.50K | 8.25K | 8.66K |
|---|---|---|---|---|---|---|---|---|---|---|---|---|---|---|
| | Hex Counts | 8C4 | 932 | 9C5 | A2C | A96 | B09 | B81 | BFB | C7E | D09 | D98 | ECB | F73 |
| 1.00K | 333 | MM0339 | MM0365 | MM0391 | MM0417 | MM0443 | MM0469 | MM0495 | MM0521 | MM0547 | MM0573 | MM0599 | MM0625 | MM0651 |
| 1.24K | 395 | MM0340 | MM0366 | MM0392 | MM0418 | MM0444 | MM0470 | MM0496 | MM0522 | MM0548 | MM0574 | MM0600 | MM0626 | MM0652 |
| 1.50K | 3FF | MM0341 | MM0367 | MM0393 | MM0419 | MM0445 | MM0471 | MM0497 | MM0523 | MM0549 | MM0575 | MM0601 | MM0627 | MM0653 |
| 1.74K | 462 | MM0342 | MM0368 | MM0394 | MM0420 | MM0446 | MM0472 | MM0498 | MM0524 | MM0550 | MM0576 | MM0602 | MM0628 | MM0654 |
| 2.00K | 4CC | MM0343 | MM0369 | MM0395 | MM0421 | MM0447 | MM0473 | MM0499 | MM0525 | MM0551 | MM0577 | MM0603 | MM0629 | MM0655 |
| 2.21K | 522 | MM0344 | MM0370 | MM0396 | MM0422 | MM0448 | MM0474 | MM0500 | MM0526 | MM0552 | MM0578 | MM0604 | MM0630 | MM0656 |
| 2.49K | 595 | MM0345 | MM0371 | MM0397 | MM0423 | MM0449 | MM0475 | MM0501 | MM0527 | MM0553 | MM0579 | MM0605 | MM0631 | MM0657 |
| 2.74K | 5FB | MM0346 | MM0372 | MM0398 | MM0424 | MM0450 | MM0476 | MM0502 | MM0528 | MM0554 | MM0580 | MM0606 | MM0632 | MM0658 |
| 3.09K | 68B | MM0347 | MM0373 | MM0399 | MM0425 | MM0451 | MM0477 | MM0503 | MM0529 | MM0555 | MM0581 | MM0607 | MM0633 | MM0659 |
| 3.32K | 6E9 | MM0348 | MM0374 | MM0400 | MM0426 | MM0452 | MM0478 | MM0504 | MM0530 | MM0556 | MM0582 | MM0608 | MM0634 | MM0660 |
| 3.65K | 770 | MM0349 | MM0375 | MM0401 | MM0427 | MM0453 | MM0479 | MM0505 | MM0531 | MM0557 | MM0583 | MM0609 | MM0635 | MM0661 |
| 3.92K | 7DE | MM0350 | MM0376 | MM0402 | MM0428 | MM0454 | MM0480 | MM0506 | MM0532 | MM0558 | MM0584 | MM0610 | MM0636 | MM0662 |
| 4.22K | 859 | MM0351 | MM0377 | MM0403 | MM0429 | MM0455 | MM0481 | MM0507 | MM0533 | MM0559 | MM0585 | MM0611 | MM0637 | MM0663 |
| 4.48K | 8C4 | MM0352 | MM0378 | MM0404 | MM0430 | MM0456 | MM0482 | MM0508 | MM0534 | MM0560 | MM0586 | MM0612 | MM0638 | MM0664 |
| 4.75K | 932 | MM0353 | MM0379 | MM0405 | MM0431 | MM0457 | MM0483 | MM0509 | MM0535 | MM0561 | MM0587 | MM0613 | MM0639 | MM0665 |
| 5.11K | 9C6 | MM0354 | MM0380 | MM0406 | MM0432 | MM0458 | MM0484 | MM0510 | MM0536 | MM0562 | MM0588 | MM0614 | MM0640 | MM0666 |
| 5.36K | A2C | MM0355 | MM0381 | MM0407 | MM0433 | MM0459 | MM0485 | MM0511 | MM0537 | MM0563 | MM0589 | MM0615 | MM0641 | MM0667 |
| 5.62K | A96 | MM0356 | MM0382 | MM0408 | MM0434 | MM0460 | MM0486 | MM0512 | MM0538 | MM0564 | MM0590 | MM0616 | MM0642 | MM0668 |
| 5.90K | B09 | MM0357 | MM0383 | MM0409 | MM0435 | MM0461 | MM0487 | MM0513 | MM0539 | MM0565 | MM0591 | MM0617 | MM0643 | MM0669 |
| 6.19K | B81 | MM0358 | MM0384 | MM0410 | MM0436 | MM0462 | MM0488 | MM0514 | MM0540 | MM0566 | MM0592 | MM0618 | MM0644 | MM0670 |
| 6.49K | BFB | MM0359 | MM0385 | MM0411 | MM0437 | MM0463 | MM0489 | MM0515 | MM0541 | MM0567 | MM0593 | MM0619 | MM0645 | MM0671 |
| 6.81K | C7E | MM0360 | MM0386 | MM0412 | MM0438 | MM0464 | MM0490 | MM0516 | MM0542 | MM0568 | MM0594 | MM0620 | MM0646 | MM0672 |
| 7.15K | D09 | MM0361 | MM0387 | MM0413 | MM0439 | MM0465 | MM0491 | MM0517 | MM0543 | MM0569 | MM0595 | MM0621 | MM0647 | MM0673 |
| 7.50K | D98 | MM0362 | MM0388 | MM0414 | MM0440 | MM0466 | MM0492 | MM0518 | MM0544 | MM0570 | MM0596 | MM0622 | MM0648 | MM0674 |
| 8.25K | ECB | MM0363 | MM0389 | MM0415 | MM0441 | MM0467 | MM0493 | MM0519 | MM0545 | MM0671 | MM0597 | MM0623 | MM0649 | MM0675 |
| 8.66K | F73 | MM0364 | MM0390 | MM0416 | MM0442 | MM0468 | MM0494 | MM0520 | MM0546 | MM0572 | MM0598 | MM0624 | MM0650 | MM0676 |

FIG. 3b Valid MMLC-type Accessory Codes for Slot #3 (Codes are for Slot #3/contact #4; MM0...type shown)

METHOD AND SYSTEM FOR VERIFICATION OF DIFFERENT TYPES OF BEAM LIMITING DEVICES IN A LINEAR ACCELERATOR UTILIZED FOR RADIOTHERAPY

This application claims the benefit of U.S. provisional application No. 60/158,553, filed Oct. 6, 1998.

FIELD OF THE INVENTION

The present invention relates generally to beam limiting devices in radiation therapy devices and more particularly to providing a variety of beam limiting devices on such devices.

BACKGROUND OF THE INVENTION

Beam limiting devices such as, third party mini-multileaf collimator (MMLC) are typically utilized as accessories with linear accelerators for radiotherapy. These MMLCs are used primarily for radiosurgery and conformal radiotherapy. As their name implies, mini-multileaf collimators provide finer resolution for matching a treatment area shape than standard multileaf collimators, e.g., 0.5 cm resolution rather than 1.0 cm resolution. By providing this finer resolution, more precision is achieved for certain treatment areas, such as the brain. Even with a finer resolution, accurate collimator positioning remains vital for ensuring that only the desired treatment area is subjected to radiation.

Accordingly, what is needed is a system and method for supporting third party beam limiting devices that ensures accuracy for positioning of the beam limiting device. The present invention addresses such a need.

SUMMARY OF THE INVENTION

The present invention provides method and system aspects for verifying an accessory beam limiting device position for a radiotherapy treatment session. Included in a system aspect is a radiotherapy treatment device, the radiotherapy treatment device including an accessory holder. A beam limiting device for establishing a treatment area, the beam limiting device held in the accessory holder, is also included, along with a first controller for controlling the radiotherapy device and performing a treatment plan. A second controller positions the beam limiting device according to the treatment plan, wherein performance of the treatment plan by the first controller depends on provision of an accessory code to the first controller. The accessory code includes a resistor-pair combination value.

Through the present invention, a code, representing values for a resistor-pair combination, is provided for third party beam limiting devices, particularly MMLCs. Improper positioning of the MMLCs results in a code that represents a 'not-ready' condition for the MMLCs and stalls the performance of the treatment session. Thus, proper positioning of the accessory beam limiting device is ensured in a straightforward and efficient manner before radiation is delivered. These and other advantages of the present invention will be more fully understood in conjunction with the following detailed description and accompanying drawings.

BRIEF DESCRIPTION OF THE DRAWINGS

FIG. 2 is a table illustrating a Slot #3/Contact #3 Encoding for valid MMMx-type Codes.

FIGS. 3a and 3b illustrate valid MMLC-Type Accessory Codes for Slot #3.

DETAILED DESCRIPTION OF THE INVENTION

Definitions, Acronyms and Abbreviations

Figure 1:
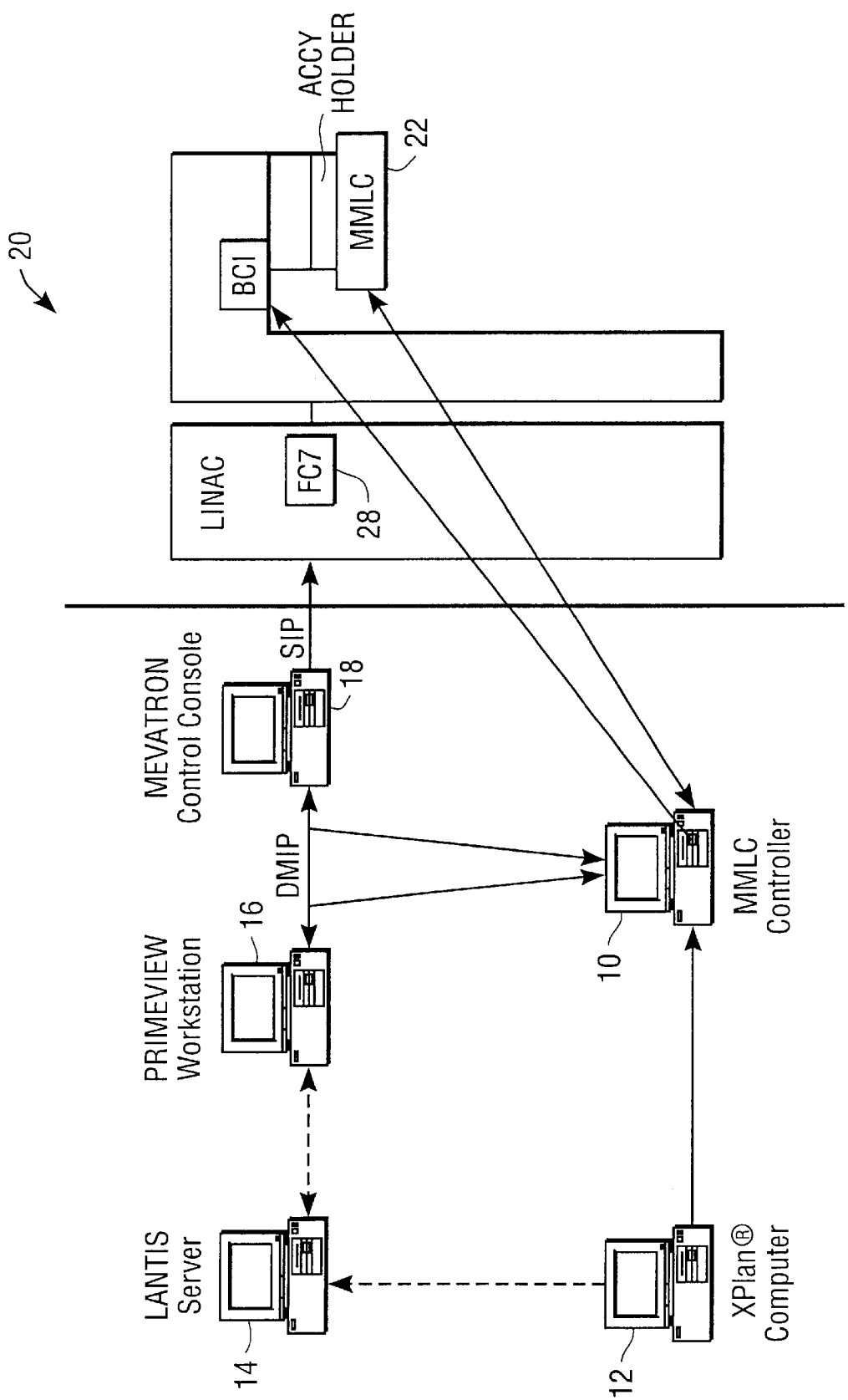
FIG. 1 is an overall system block diagram in accordance with the present invention.

BCI is the abbreviation for a third party Block Code Interface.

FRS is the abbreviation for Functional Requirements Specifications.

IL is the abbreviation for Interlock asserted by Mevatron.

Lantis® is the abbreviation for Local Area Network Therapy Information System or any other information management system.

MMLC is the term for a third party mini-multileaf collimator.

PID is a term for Patient Identification.

Primeview® is the term for the SMS-OCS record and verify system.

SDS is the abbreviation for System Design Specification.

SRS is the abbreviation for Software Requirement Specification.

XPlan® is the trademark for the third party Treatment Planning Software.

The present invention relates generally to collimators in radiation therapy devices and more particularly to providing proper positioning with a variety of collimators on such devices. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

FIG. 1 is an overall system block diagram in accordance with the present invention. It should be appreciated that the names and types of system are meant to be exemplary and not restrictive of the elements in which the present invention has application. Particularly, the following description refers to the verification of positioning of MMLCs. However, MMLCs represent one type of beam limiting device for which the aspects of the present invention find particular utilization. One of ordinary skill in the art recognizes a variety of beam limiting devices, for example a rod device, could be utilized and then we would be within the spirit and scope of the present invention. Referring to FIG. 1, the system includes a plurality of control mechanisms, including an MMLC controller 10, an XPlan computer 12, a Lantis server 14, a Primeview workstation 16, and a Mevatron control console 18, and a radiotherapy device 20, including a linear accelerator (LINAC). In FIG. 1, dashed lines indicate network communications, light solid lines represent proprietary communication protocols, and heavy solid lines represent hard wired connections.

Functional Description

XPlan and Lantis Server

The XPlan computer 12 generates the MMLC treatment plan which is transmitted in RTP Link file format to the Lantis server 14 and to the MMLC controller 10. An MMLC treatment plan for a particular patient includes a patient ID and a single field or set of fields. Treatment plans are then transmitted to Primeview for treatment execution. All the treatment parameters are specified in the treatment plan except the actual third party MMLC leaf positions, since there is currently no provision to store them in Lantis server 14. The Lantis server 14 acts as the SMS-OCS Verify and Read (V&R) system. Each field of the treatment plan transmitted to the Lantis server 14 and then the Primeview workstation 16 will specify the gantry and collimator angles, table position and other dosimetry information for the treatment session. The XPlan computer 12 assigns a unique MMLC-type accessory coding to each field of an MMLC treatment plan.

MMLC Controller

The MMLC controller 10 listens and decodes all the DMIP packet exchanges between Primeview workstation 16 and the Mevatron control console 18. Upon the detection of an MMLC treatment field in the treatment setup download packet, the MMLC controller 10 sets the MMLC 22 into position according to the required field in the downloaded packet and waits until the MMLC 22 leaves are set. In setting the MMLC 22 leaves, the MMLC controller 10 verifies the position. An accessory code, i.e., a resistor-pair combination, provides an indication of the positioning of and aperture size of the MMLC 22 and is provided to the Mevatron control console 18 via the BCI component 26. Any abnormal condition detected by the MMLC controller 10 will cause it to present a resistor-pair combination which defines a "not-ready" accessory code to the Mevatron control console 18 thereby preventing further action in the treatment routine until the abnormality is cleared or when the treatment is cancelled.

Block Code Interface Component (BCI)

The BCI component 26 provides the interface between the MMLC controller 10 and the Mevatron control console 18 via a BCI/G41 37-pin adapter cable. The BCI 26 is mounted in the gantry area with close proximity to the G41 card cage, as is well appreciated by those skilled in the art. Upon command from the MMLC controller 10, the BCI 26 presents the specified resistor-pair combination to the Mevatron's 22 accessory code channels for slot #3 (i.e., the slot within which the MMLC 22 is held) to display the corresponding MMLC-type accessory code.

Third Party Mini-multileaf Collimator (MMLC)

The third party MMLC 22 is a computer controlled conformal radiation therapy device. By way of example, a third party MMLC 22 has 62 leaves and each leaf projects to 4.0 mm width at isocenter with a maximum field size of 10 cm by 12 cm. As shown, the third party MMLC 22 is mounted in a slot of the accessory holder 24.

Accessory Holder

A modification of a standard accessory holder provides easy adaptation for third party MMLC and non-MMLC type treatments. A "split-design" feature allows use of the same accessory holder base and physical slot #3 where the MMLC 22 is mounted. The modification of accessory holder 24 preferably also allows insertion of other SMS-OCS standard accessories in slots #1 and #2 but does not allow any SMS-OCS slot #3 accessory when it is in the "third party MMLC" configuration.

Primeview

The Primeview workstation 16 provides the SMS-OCS verify and record graphical user interface, which gives a graphical presentation of treatment parameters to be delivered. New types of accessory codes support the third party MMLC, as described further hereinbelow.

Mevatron Control Console Software

The control console software of the Mevatron control console 18 provides the support for the third party MMLC accessory coding scheme as well as for MMLC interlock functionality. When necessary, the control console 18 asserts an error signal, e.g., IL 19, Accessory Read Fault with the presence of MML-NR code, which holds in all states. To accommodate new third party accessory codes, new resistor-pair combination values are allowed in slot #3, i.e., in contacts #3 and #4 of the accessory channel. To allow for numerous block codes for the third party MMLC, the valid accessory codes take the form of MMxyyy where 'x' ranges from 0 through 8 depending on the resistor-pair (RA and RB) combination in slot #3/contact #3 and 'yyy' ranges from 001 to 676 on the resistor-pair (RA and RB) combination in slot#3/contact#4. The values of the resistor-pair for slot#3/contact #3 are presented in FIG. 2.

FIGS. 3a and 3b illustrate valid MMLC-Type Accessory Codes for Slot #3. With a valid MMLC-type resistor-pair combination in slot #3/contact #3, the console software of control console 18 allows the resistor-pair combination values in slot#3/contact#4 to decode valid MMLC accessory codes as listed in FIGS. 3a and 3b. (These figures show MM0001 through MM0676 valid accessory coding only.)

I/O Function Controller (FC 7)

The function controller 28 is responsible for the reading and reporting of the accessory code values in the Mevatron control console 18 via SIP communication. A new functionality in autosequence treatment delivery could be used to allow changes in an accessory code during a Pause state.

Through the present invention, a code, representing values for a resistor-pair combination, is provided for third party beam limiting devices, particularly MMLCs. Improper positioning of the MMLCs results in a code that represents a 'not-ready' condition for the MMLCs and stalls the performance of the treatment session. Thus, proper positioning of the accessory beam limiting device is ensured in a straightforward and efficient manner before radiation is delivered.

Although the present invention has been described in accordance with the embodiments shown, one of ordinary skill in the art will readily recognize that there could be variations to the embodiments and those variations would be within the spirit and scope of the present invention. Accordingly, many modifications may be made by one or ordinary skill in the art without departing from the spirit and scope of the appended claims.

What is claimed is:

1. A system for verifying an accessory beam limiting device position for a radiotherapy treatment session, the system comprising:
    a radiotherapy treatment device, the radiotherapy treatment device including an accessory holder;
    a beam limiting device for establishing a treatment area, the beam limiting device held in the accessory holder;
    a first controller for controlling the radiotherapy device and performing a treatment plan; and
    a second controller for positioning the beam limiting device based on the treatment plan, wherein performance of the treatment plan by the first controller depends on provision of an accessory code from the second controller to the first controller, the accessory code comprising a resistor-pair combination value.

2. The system of claim 1 wherein the beam limiting device further comprises a mini-multileaf collimator (MMLC).

3. The system of claim 1 wherein the first controller performs the treatment plan when the accessory code indicates a valid position code for the beam limiting device.

4. The system of claim 1 wherein the first controller holds the radiotherapy treatment device in a not-ready state when the accessory code indicates a not-ready condition for the beam limiting device.

5. A method for verifying an accessory beam limiting device position for a radiotherapy treatment session, the method comprising:

transmitting a treatment plan to a radiotherapy control device;

setting an accessory beam limiting device into position based on the treatment plan; and verifying the position according to a resistor-pair combination to control performance of the treatment plan.

6. The method of claim 5 wherein setting an accessory beam limiting device further comprises setting a mini-multileaf collimator (MMLC).

7. The method of claim 6 wherein setting an accessory beam limiting device further comprises setting by an MMLC controller system.

8. A method for verifying an accessory beam limiting device position for a radiotherapy treatment session, the method comprising:

transmitting a treatment plan to a radiotherapy control device;

setting an accessory beam limiting device into position based on the treatment plan; and verifying the position according to a resistor-pair combination to control performance of the treatment plan, wherein when the resistor-pair combination provides a not-ready predefined code, performance of the treatment plan is stalled.

9. A system for controlling positioning of an accessory beam limiting device in a radiotherapy device, the system comprising:

a first control means for positioning an accessory beam limiting device into position based on a treatment plan and identifying an accessory code comprising a resistor-pair combination for the accessory beam limiting device; and a second control means coupled to the first control means and performing a treatment plan in the radiotherapy device when the first control means provides a valid accessory code.

10. The system of claim 9 wherein the accessory beam limiting device further comprises a mini-multileaf collimator.

11. The system of claim 9 wherein the first control means verifies the position of the accessory beam limiting device by detecting contact resistor values for the accessory beam limiting device.

12. The system of claim 11 wherein when the contact resistor values are improper, the second control means holds the radiotherapy device in a not-ready condition.

13. A system for verifying an accessory beam limiting device position for a radiotherapy treatment session, the system comprising:

a radiotherapy treatment device, the radiotherapy treatment device including an accessory holder;

a beam limiting device for establishing a treatment area, the beam limiting device held in the accessory holder;

a first controller for controlling the radiotherapy device and performing a treatment plan; and a second controller for positioning the beam limiting device based on the treatment plan, wherein performance of the treatment plan by the first controller depends on provision of a resistor pair combination from the second controller to the first controller, the resistor pair combination being related to the aperture size of the beam limiting device.

14. The system of claim 13 wherein the beam limiting device further comprises a mini-multileaf collimator (MMLC).

15. The system of claim 13 wherein the first controller performs the treatment plan when the resistor pair combination indicates a valid position code for the beam limiting device.

16. The system of claim 13 wherein the first controller holds the radiotherapy treatment device in a not-ready state when the resistor pair combination indicates a not-ready condition for the beam limiting device.

* * * * *